(12) United States Patent
Ergen et al.

(10) Patent No.: US 9,143,927 B2
(45) Date of Patent: Sep. 22, 2015

(54) METHOD AND APPARATUS FOR MANAGING CONNECTION IDENTIFIERS (CIDS) IN A WIRELESS COMMUNICATION NETWORK

(75) Inventors: Mustafa Ergen, Oakland, CA (US);
Rehan Jalil, San Jose, CA (US)

(73) Assignee: WiChorus Inc., Santa Clara, CA (US)

( * ) Notice: Subject to any disclaimer, the term of this patent is extended or adjusted under 35 U.S.C. 154(b) by 1927 days.

(21) Appl. No.: 12/198,906

(22) Filed: Aug. 27, 2008

(65) Prior Publication Data
US 2009/0061922 A1 Mar. 5, 2009

Related U.S. Application Data

(60) Provisional application No. 60/966,509, filed on Aug. 27, 2007.

(51) Int. Cl.
*H04W 8/26* (2009.01)
*H04W 36/08* (2009.01)
(52) U.S. Cl.
CPC ............ *H04W 8/26* (2013.01); *H04W 36/08* (2013.01)
(58) Field of Classification Search
CPC ................................. H04W 8/26; H04W 36/08
USPC .................. 455/436–445, 524–525; 370/331
See application file for complete search history.

(56) References Cited

U.S. PATENT DOCUMENTS

| | | | |
|---|---|---|---|
| 7,720,088 B2 * | 5/2010 | Wu | 370/442 |
| 2007/0097945 A1 * | 5/2007 | Wang et al. | 370/349 |
| 2007/0149123 A1 * | 6/2007 | Palin | 455/41.2 |
| 2007/0211726 A1 * | 9/2007 | Kuang et al. | 370/395.3 |
| 2009/0016297 A1 * | 1/2009 | Lee | 370/331 |

* cited by examiner

*Primary Examiner* — Raymond Dean
(74) *Attorney, Agent, or Firm* — Hamilton, Brook, Smith & Reynolds, P.C.

(57) ABSTRACT

A method and apparatus for managing communication in a wireless communication network is provided. The method includes generating a plurality of sets of Connection Identifiers (CIDs) from the plurality of CIDs. Each CID in each of the plurality of sets of CIDs is absent in at least one of the plurality of sets of CIDs. Each CID of the plurality of CIDs identifies a connection between a Base Station (BS) of a plurality of BSs and a Mobile Station (MS) communicating with the BS. The method further includes assigning the plurality of sets of CIDs to the plurality of Base stations (BSs) in the wireless communication network based on a predefined condition.

33 Claims, 8 Drawing Sheets

METHOD AND APPARATUS FOR MANAGING CONNECTION IDENTIFIERS (CIDS) IN A WIRELESS COMMUNICATION NETWORK

RELATED APPLICATIONS

Benefit is claimed under 35 U.S.C. 119(e) to U.S. Provisional Application Ser. No. 60/966,509 entitled "A method and apparatus for managing connection identifiers (CIDs) in a wireless communication network" by Mustafa Ergen et al., filed on 27 Aug. 2007, which is herein incorporated in its entirety by reference for all purposes.

FIELD OF THE INVENTION

The invention generally relates to a wireless communication network. More specifically, the invention relates to a method and apparatus for managing Connection Identifiers (CIDs) a wireless communication network. Examples of the wireless communication network may include, but are not limited to a Worldwide Interoperability for Microwave Access (WiMAX) communication network, a 3rd Generation Partnership Project (3GPP) network including a 3GPP Long Term Evolution (LTE) network, a 3rd Generation Partnership Project 2 (3GPP2) network including a 3GPP2 Ultra Mobile Broadband (UMB) network, as well as a Wireless Fidelity (WiFi) network, and any variant of Orthogonal Frequency Division Multiple Access (OFDMA) communication network having a backhaul link.

BACKGROUND OF THE INVENTION

A wireless communication network includes a plurality of Access Service Network Gateway (ASN-GWs). The plurality ASN-GWs controls a plurality of Base Stations (BSs). One or more BSs communicate with an associated ASN-GW of the plurality of ASN-GWs to access a plurality of services. The plurality of services may include, but are not limited to, video distribution, vehicle tracking, e-learning, file sharing, web browsing, and weather monitoring. An ASN-GW communicates the plurality of services to one or more BSs associated with the ASN-GW as one or more data packets. The one or more data packets are classified into a plurality of data service flows. Each data service flow is assigned a Service Flow ID (SFID) by the ASN-GW. A SFID assigns a service flow of packets to a MS and a BS. In a Worldwide Interoperability for Microwave Access (WiMAX) communication network, the SFID is a 32 bit value. After receiving the one or more data packets from the ASN-GW, each BS of the one or more BSs communicates the one or more data packets to a corresponding MS of a set of MSs assigned to each BS. In order to communicate the one or more data packets to the corresponding MS, a BS assigns a Connection Identifiers (CIDs) to each MS in the set of MSs communicating with the BS. A CID identifies a connection between a BS and a MS. In the WiMAX communication network, the CID is a 16 bit value. Thereafter, the one or more data packets are communicated to the corresponding MS by the BS by mapping the SFID of the data service flows to the CID assigned to the MS.

In a wireless communication network, a MS may be handovered from a source BS to a target BS. During handover, a first CID assigned to the MS by the source BS may be similar to a second CID assigned to a second MS by the target BS. This conflict occurs as a total number of CIDs present in the wireless communication system is less than a total number of SFIDs present in the wireless communication system. Additionally, a plurality of CIDs is assigned to one or more MSs locally by the one or more BS. Therefore, there is an increased possibility that a CID may be assigned to multiple MSs in the wireless communication network.

There is therefore a need of a method and apparatus for managing CIDs in the wireless communication network such that the conflict during handover of a MS from a source BS to a target BS can be avoided.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the invention.

DETAILED DESCRIPTION OF THE INVENTION

Before describing in detail embodiments that are in accordance with the invention, it should be observed that the embodiments reside primarily in combinations of method steps and apparatus components related to managing a plurality of Connection Identifiers (CIDs) in a wireless communication network. Accordingly, the apparatus components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Various embodiments of the invention provide methods and apparatuses for managing a plurality of Connection Identifiers (CIDs) in a wireless communication network. Examples of the wireless communication network may include, but are not limited to a Worldwide Interoperability for Microwave Access (WiMAX) communication network, a 3rd Generation Partnership Project (3GPP) network including 3GPP Long Term Evolution (LTE) network, a 3rd Generation Partnership Project 2 (3GPP2) network including 3GPP2 Ultra Mobile Broadband (UMB) network, a Wireless Fidelity (WiFi) network, and any variant of Orthogonal Frequency Division Multiple Access (OFDMA) communication. The method includes generating a plurality of sets of CIDs from the plurality of CIDs. Each CID in each of the plurality of sets of CIDs is absent in one or more of the plurality of sets of CIDs. The method further includes assigning the plurality of sets of CIDs to a plurality of Base Stations (BSs) based on a predefined condition. It will be apparent to a person skilled in the art the invention is equally applicable to other IDs (equivalent to a CID) used in various wireless communication networks.

Figure 1:
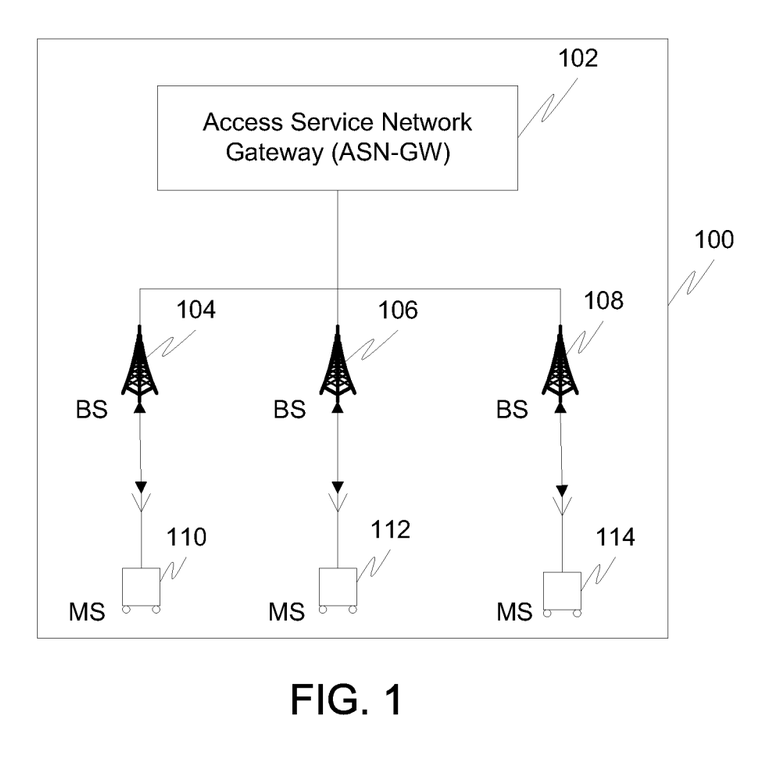
FIG. 1 is a block diagram showing a wireless communication network (that is exemplary) in which various embodiments of the invention may function.

FIG. 1 is block diagram showing a wireless communication network 100 (that is exemplary) in which various embodiments of the invention may function. Wireless communication network 100 may be a Worldwide Interoperability for Microwave Access (WiMAX) communication network. Wireless communication network 100 includes an ASN-GW 102. Further, ASN-GW 102 communicates with a plurality of Base Stations (BSs) (for example a BS 104, a BS 106, and a BS 108). It will be apparent to a person skilled in the art that wireless communication network 100 may include more than one ASN-GW. Each BS of the plurality of BSs communicates with one or more Mobile Stations (MSs). For example, BS 104 communicates with a MS 110, BS 106 communicates with a MS 112, and BS 108 communicates with a MS 114. Examples of a MS may include, but are not limited to a laptop, a computer, a Personal Digital Assistant (PDA), and a hand-held device. A subscriber uses a MS to avail communication services over wireless connectivity through a corresponding BS.

ASN-GW 102 transfers data as one or more packets to the plurality of BSs. The data may include, but is not limited to video distribution, vehicle tracking, e-learning, file sharing, web browsing, and weather monitoring. Before transmission, ASN-GW 102 classifies the one or more packets into a plurality of data service flows. Each data service flow is assigned a Service Flow ID (SFID) by ASN-GW 102. A SFID assigns a data service flow of packets to a MS and a BS. In a WiMAX communication network, the SFID is a 32-bit value. Thereafter, the plurality of BSs communicate the one or more packets to the one or more MSs. This is achieved by mapping a SFID of a data service flow of the plurality of data service flows to a Connection Identifier (CID) assigned to a MS. A CID is a value that identifies a connection between a BS and a MS. A CID is assigned by a BS to a MS associated with the BS. In a WiMAX communication network, the CID is a 16 bit value. It will be apparent to a person skilled in the art the invention is equally applicable to other IDs (equivalent to a CID) used in various wireless communication networks.

Figure 2:
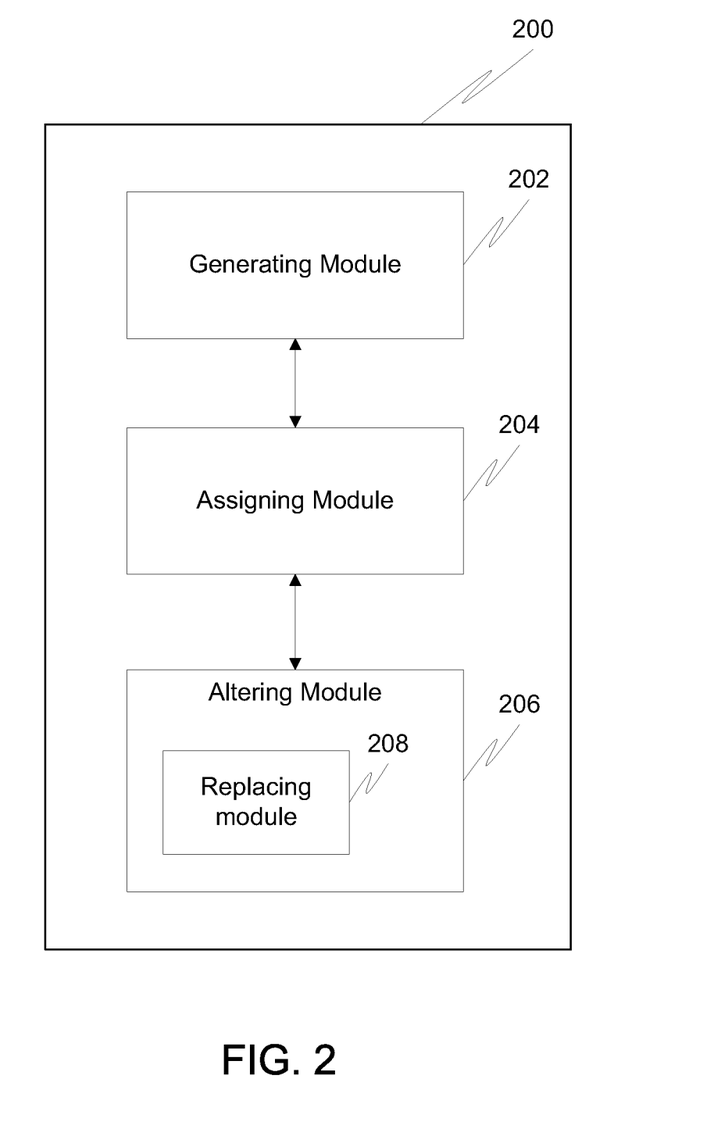
FIG. 2 is a block diagram showing a system for managing a plurality of Connection Identifiers (CIDs) in a wireless communication network, in accordance with an embodiment of the invention.

FIG. 2 is a block diagram showing a system 200 for managing a plurality of CIDs in wireless communication network 100, in accordance with an embodiment of the invention. System 200 includes a generating module 202 and an assigning module 204. Generating module 202 generates a plurality of sets of CIDs from the plurality of CIDs. Each CID in each of the plurality of sets of CIDs is absent in one or more of the plurality of sets of CIDs. In a first scenario, each CID in each of the plurality of sets of CIDs may be unique. For example, generating module 202 generates three sets of CIDs, namely a first set of CIDs, a second set of CIDs, and a third set of CIDs from six CIDs. The first set of CIDs includes a CID-1 and a CID-2, the second set of CIDs includes a CID-3 and a CID-4, and the third set of CIDs includes a CID-5 and a CID-6. Therefore, each CID in the first set of CIDs, the second set of CIDs, and the third set of CIDs is unique. Alternatively, in another scenario, one or more CIDs in one or more sets of CIDs of the plurality of sets of CIDs may be common. For example, generating module 202 generates three sets of CIDs, i.e., a first set of CIDs, a second set of CIDs, and a third set of CIDs from five CIDs. The first set of CIDs includes a CID-1 and a CID-2, the second set of CIDCIDs includes a CID-3 and a CID-4, and the third set of CIDs includes a CID-4 and a CID-5. In this example, the CID-4 is common to each of the second set of CIDs and the third set of CIDs.

Thereafter, assigning module 204 assigns the plurality of sets of CIDs to a plurality of BSs based on a predefined condition. The predefined condition is a distance between the plurality of BSs. In this case, the plurality of sets of CIDs are assigned based on the distance between the plurality of BSs. This is further explained in detail in conjunction with FIG. 3. If each CID in each of the plurality of sets of CIDs is unique, then assigning module 204 assigns the plurality of CIDs to the plurality of BSs irrespective of the distance between the plurality of BSs. For example, a first set of CIDs may include a CID-1 and a CID-2, a second set of CIDs may include a CID-3 and a CID-4. Each CID in the first set of CIDs and the second set of CIDs are unique. Therefore, the first set of CIDCIDs may be assigned to a first BS of the plurality of BSs and the second set of CIDs may be assigned to a second BS of the plurality of BSs, which is collocated with the first BS. As each CID in each of the first set of CIDs and the second set of CIDs is unique, therefore, a CID conflict will not occur during a handover situation between the first BS and the second BS.

In wireless communication network 100, when a MS of a plurality of MSs is handovered from a serving BS of the plurality of BSs to a target BS of the plurality of BSs, an altering module 206 alters a first set of CIDs of the plurality of sets of CIDs assigned to the target BS. A first CID of the first set of CIDs assigned to the target BS and a second CID assigned to the MS by the serving BS may be same. After handover of the MS, the target BS may be serving two MS having the same CID. This may result in a conflict of the first CID and the second CID, which may further lead to interference in communication of the MS with the target BS. To avoid this conflict, the first set of CIDs is altered by a replacing module 208 that replaces the first CID with a third CID. The third CID is selected from a second set of CIDs of the plurality of sets of CIDs. The second set of CIDs is assigned to a BS in the plurality of BSs. The distance between the target BS and the BS is maximum. Therefore, the third CID selected from the second set of CIDs assigned to the BS can be reused to replace the first CID, as the BS and the target BS are not collocated and also there will not be a handover situation between the BS and the target BS. In an embodiment, the third CID in the second set of CIDs may be unused by any MS served by the BS.

For example, in wireless communication network 100, BS 104 is assigned a first set of CIDs, which includes a CID-1 and a CID-2. BS 106 is assigned a second set of CIDs, which includes the CID-1 and a CID-3. Similarly, BS 108 is assigned a third set of CIDs, which includes a CID-4 and a CID-5. Among BS 104, BS 106, and BS 108, the distance between BS 104 and BS 108 is maximum. Thereafter, BS 104 assigns the CID-1 to MS 110, BS 106 assigns the CID-1 to MS 112, and BS 108 assigns the CID-4 to MS 114. Initially, MS 112 is served by BS 106. However, MS 112 may be handovered to BS 104, as a result of which a conflict occurs as each of MS 112 and MS 110 is assigned the same CID, i.e., the CID-1. Therefore, in order to avoid the conflict, the first set of CIDs assigned to BS 104 is altered by replacing the CID-1 in the first set of CIDs with the CID-4 assigned to MS 114. The CID-4 assigned to MS 114 is reused as the distance between BS 104 and BS 108 is maximum.

Figure 3:
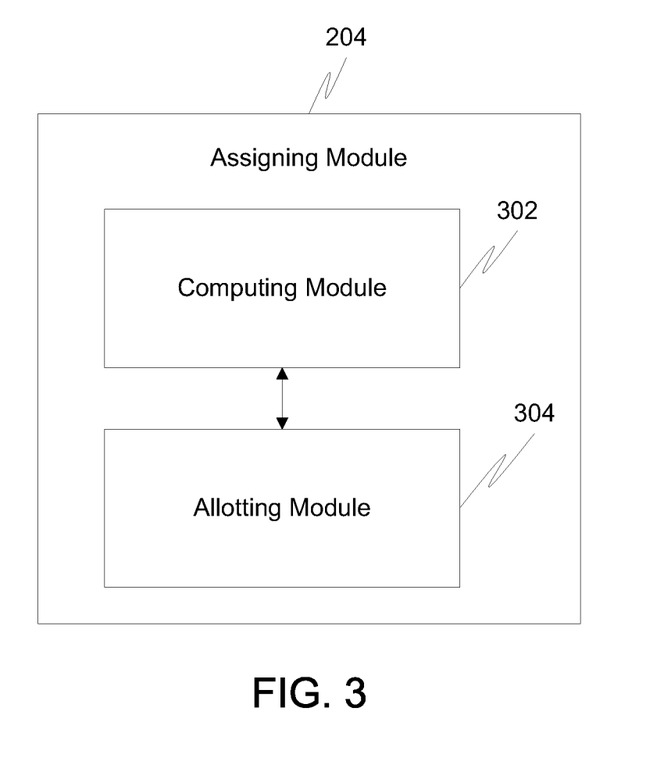
FIG. 3 is a block diagram showing various modules of an assigning module, in accordance with an embodiment of the invention.

FIG. 3 is a block diagram showing various modules of assigning module 204, in accordance with an embodiment of the invention. Assigning module 204 includes a computing module 302 and an allotting module 304. Referring back to FIG. 2, the predefined condition for assigning a plurality of sets of CIDs to a plurality of BSs is the distance between the plurality of BSs. The distance between the plurality of BSs is computed by computing module 302. Thereafter, allotting module 304 allots one or more sets of CIDs of the plurality of sets of CIDs to a set of BSs selected from the plurality of BSs. The one or more sets of CIDs include one or more common CIDs. The distance between the set of BSs is maximum.

For example, a first set of CIDs may include a CID-1 and a CID-2, a second set of CIDs may include the CID-2 and a CID-3. The CID-2 is common to each of the first set of CIDs and the second set of CIDs. Therefore, the first set of CIDs is assigned to a first BS and the second set of CIDs is assigned to a second BS as the distance between the first BS and the second BS is maximum. Therefore, there are less chances of a conflict instead of the fact that the first BS and the second BS are using a common CID, as there are very less chances that a MS may be handovered from the second BS to the first BS and vice versa. This is further explained in conjunction with FIG. 8.

Figure 4:
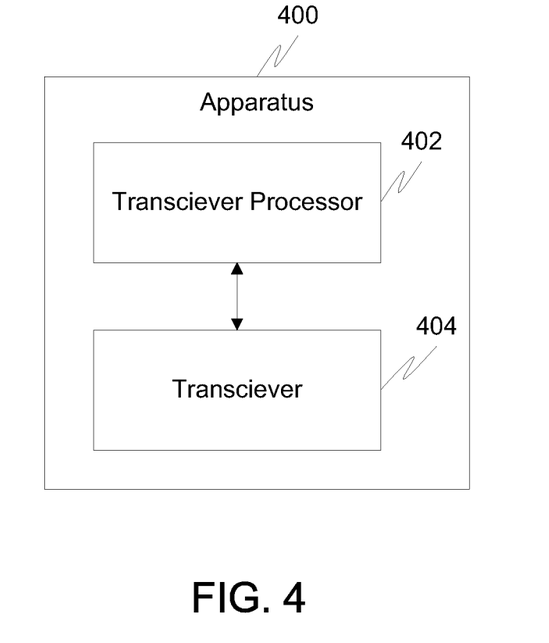
FIG. 4 is a block diagram of an apparatus for managing a plurality of CIDs in a wireless communication network, in accordance with an embodiment of the invention.

FIG. 4 is a block diagram of an apparatus 400 for managing a plurality of CIDs in wireless communication network 100, in accordance with an embodiment of the invention. Apparatus 400 includes a transceiver processor 402 and a transceiver 404. Transceiver processor 402 generates a plurality of sets of CIDs from the plurality of CIDs. Each CID in each of the plurality of sets of CIDs is absent in one or more of the plurality of sets of CIDs. Each CID in each of the plurality of sets of CIDs may be unique. Alternatively, one or more CIDs in one or more sets of CIDs of the plurality of sets of CIDs may be common. This has been explained in detail in conjunction with FIG. 2 and FIG. 3.

Thereafter, transceiver processor 402 assigns the plurality of sets of CIDs to the plurality of BSs based on a predefined condition. The predefined condition is a distance between the plurality of BSs. The distance between the plurality of BS is computed by transceiver processor 402. Thereafter, transceiver processor 402 may allot one or more sets of CIDs to a set of BSs selected from the plurality of BSs. The one or more sets of CIDs include one or more common CIDs. The distance between the set of BSs may be maximum. Transceiver 404 communicates the plurality of sets of CIDs to the plurality of sets of BSs.

In wireless communication network 100, when a MS of a plurality of MSs is handovered from a serving BS of the plurality of BSs to a target BS of the plurality of BSs, transceiver processor 402 alters a first set of CIDs of the plurality of sets of CIDs assigned to the target BS. A first CID of the first set of CIDs and a second CID assigned to the MS by the serving BS may be same. This may result in a conflict of the first CID and the second CID. Therefore, transceiver processor 402 replaces the first CID with a third CID selected from a second set of CIDs of the plurality of sets of CIDs assigned to a BS. The distance between the target BS and the BS is maximum. In an embodiment, the third CID in the second set of CIDs may be unused. This has been explained in conjunction with FIG. 2 and FIG. 3.

Apparatus 400 may be an ASN-GW. Alternatively, apparatus 400 may be a BS of the plurality of BSs. In this case, the BS communicates with ASN-GW 102 to retrieve SFIDs assigned to a plurality of data service flows. Thereafter, the BS maps a SFID of a data service flow of the plurality of data service flows to a CID assigned to a MS served by the BS. Based on this, the BS communicates one or more packets received from the ASN-GW to the plurality of BSs. Alternatively, the ASN-GW may obtain mapping information of SFIDs to CIDs from the BS, and based on that the ASN-GW may communicate one or more packets to the plurality of BS.

Figure 5:
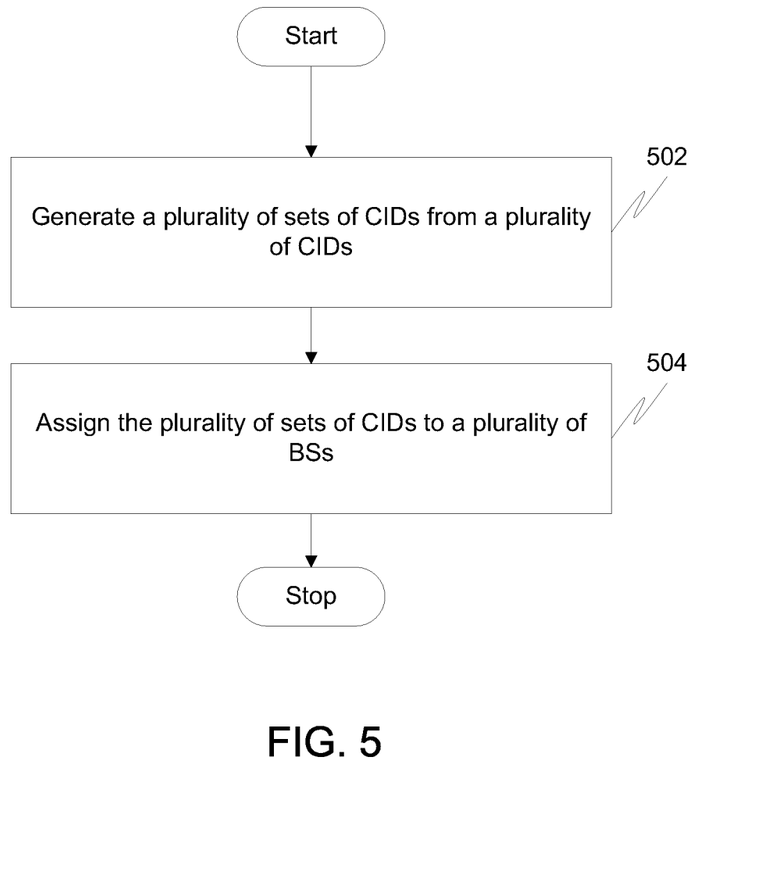
FIG. 5 is a flowchart of a method of managing a plurality of CIDs in a wireless communication network, in accordance with an embodiment of the invention.

FIG. 5 is a flowchart of a method of managing a plurality of CIDs in wireless communication network 100, in accordance with an embodiment of the invention. At step 502, the transceiver processor 402 generates a plurality of sets of CIDs from the plurality of CIDs. Each CID in each of the plurality of sets of CIDs is absent in one or more of the plurality of sets of CIDs. Each CID in each of the plurality of sets of CIDs may be unique. Alternatively, one or more CIDs in one or more sets of CIDs of the plurality of sets of CIDs may be common. This has been explained in conjunction with FIG. 2, FIG. 3 and FIG. 4.

Thereafter, the transceiver processor 402 assigns the plurality of sets of CIDs to a plurality of BSs based on a predefined condition, at step 504. This has been explained in detail in conjunction with FIG. 2, FIG. 3 and FIG. The predefined condition is a distance between the plurality of BSs. In this case, the plurality of sets of CIDs are assigned based on the distance between the plurality of BSs. This is further explained in detail in conjunction with FIG. 6.

Figure 6:
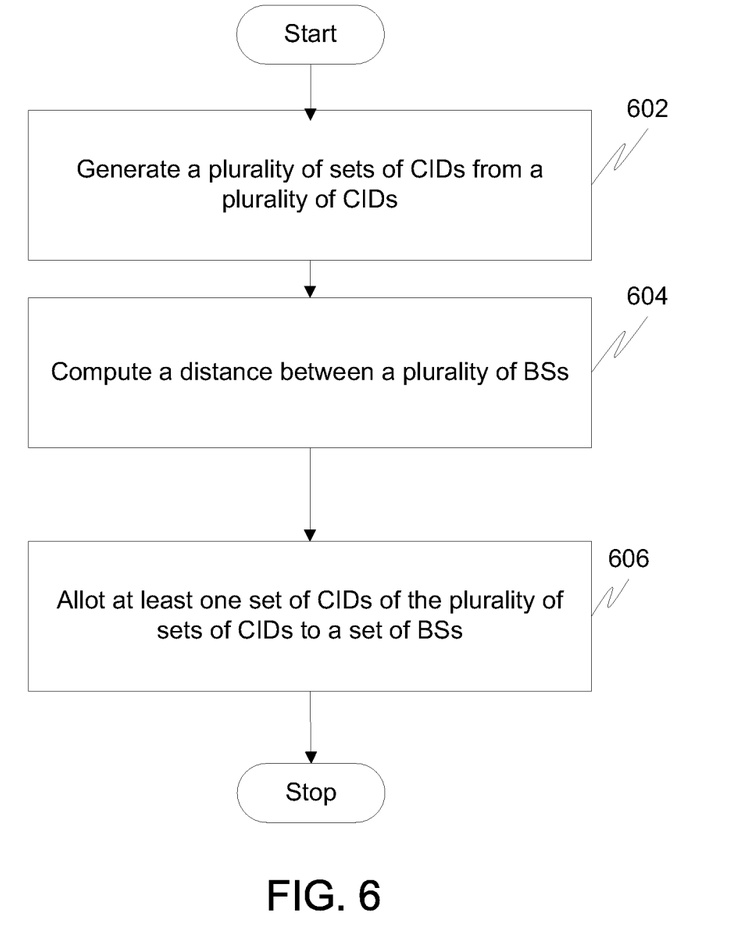
FIG. 6 is a flowchart of a method of managing a plurality of sets of CIDs in a wireless communication network, in accordance with another embodiment of the invention.

FIG. 6 is a flowchart of a method of managing a plurality of sets of CIDs in wireless communication network 100, in accordance with another embodiment of the invention. Transceiver processor 402 generates the plurality of sets of CIDs at step 602. Thereafter, transceiver processor 402 computes a distance between the plurality of BSs, at step 604. Transceiver processor 402 tracks the location of each of the plurality of BSs using one or more location detection schemes. Examples of a location detection scheme may include, but are not limited to triangulation, and trilateration. Based on this, transceiver processor 402 calculates the distance between the plurality of BSs. Alternatively, transceiver processor 402 may maintain a database which includes locations of the plurality of BSs. The locations may be recorded during setup of wireless communication network 100.

Based on computing the distance between the plurality of BSs, transceiver processor 402 selects a set of BSs of the plurality of BSs. The distance between the set of BSs is maximum. Thereafter, transceiver processor 402 allots one or more sets of CIDs of the plurality of sets of CIDs to the set of BSs at step 606. In an embodiment, the one or more sets of CIDs includes one or more common CID. This has been explained in conjunction with FIG. 3.

Figure 7:
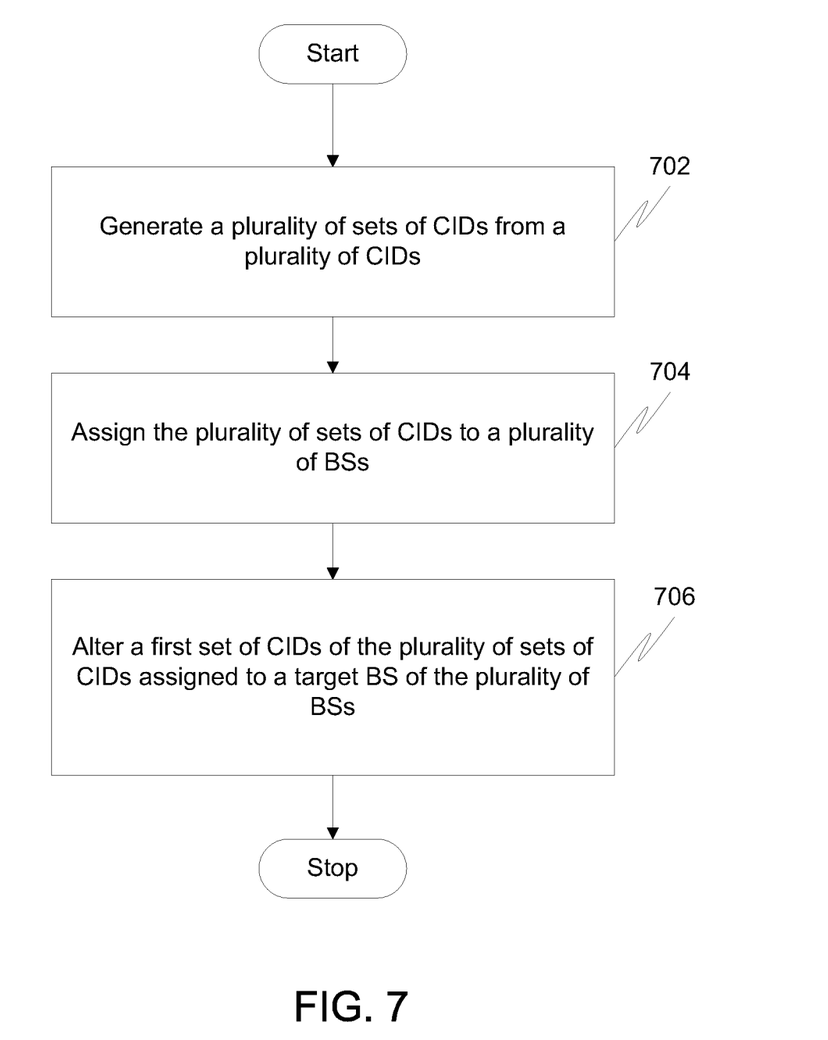
FIG. 7 is a flowchart of a method of altering a set of CID in a wireless communication network, in accordance with an embodiment of the invention.

FIG. 7 is a flowchart of a method of altering a set of CID in wireless communication network 100, in accordance with an embodiment of the invention. In accordance with FIG. 5, the transceiver processor 402 generates a plurality of sets of CIDs from a plurality of CIDs, at step 702. Thereafter, the transceiver processor 402 assigns the plurality of sets of CIDs to a plurality of BSs based on a predefined condition, at step 704. This has been explained in conjunction with FIG. 2.

In wireless communication network 100, when a MS of a plurality of MSs is handovered from a serving BS of the plurality of BSs to a target BS of the plurality of BSs, the transceiver processor 402 alters a first set of CIDs of the plurality of sets of CIDs assigned to the target BS, at step 706. A first CID of the first set of CIDs and a second CID assigned to the MS by the serving BS may be same. To alter the first set of CIDs, transceiver processor 402 replaces the first CID with a third CID which is selected from a second set of CIDs of the plurality of sets of CIDs. The second set of CIDs is assigned to a BS in the plurality of BSs. The distance between the target BS and the BS is maximum. This has been explained in detail in conjunction with FIG. 2. In an embodiment, the third CID in the second set of CIDs may be unused.

Figure 8:
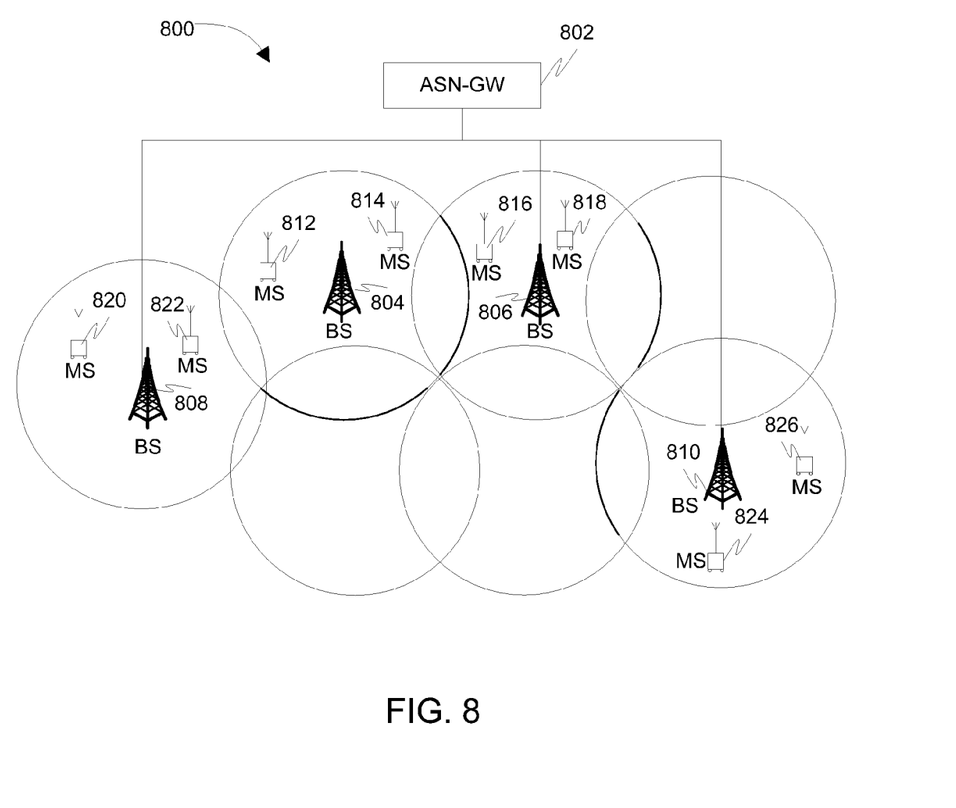
FIG. 8 depicts managing of a plurality of CIDs in a WiMAX communication network, in accordance with an exemplary embodiment of the invention Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

FIG. 8 depicts managing of a plurality of CIDs in a WiMAX communication network 800, in accordance with an exemplary embodiment of the invention. WiMAX communication network 800 includes a ASN-GW 802, a BS 804, a BS 806 and a BS 808 and a BS 810. A BS communicates with one or more Mobile Stations (MSs) operating in a coverage area of the BS. In this exemplary embodiment, BS 804 communicates with a MS 812 and a MS 814, BS 806 communicates with a MS 816 and a MS 818. Similarly, BS 808 communicates with a MS 820 and a MS 822 and BS 810 communicates with a MS 824 and a MS 826.

To initiate communication in WiMAX communication network 800, apparatus 400, which is an ASN-GW, assigns a first set of CIDs to BS 804, a second set of CIDs to BS 806, a third set of CIDs to BS 808, and a fourth set of CIDs to BS 810. The first set of CIDs includes a CID-1 and a CID-2, the second set of CIDs includes a CID-3 and a CID-4, the third set of CIDs includes a CID-5 and a CID-6, and the fourth set of CIDs includes a CID-7, the CID-1. Since each CID in the second set of CIDs and the third set of CIDs are unique, the second set of CIDs is assigned to BS 806 and the third set of CIDs is assigned to BS 808 irrespective of a distance between BS 806 and BS 808, which are collocated. Thus, a conflict of a common CID is avoided during handover of MSs served by BS 806 to BS 808. Similarly, a conflict of a common CID is avoided during handover of MSs served by BS 808 to BS 806 as each CID in the second set of CIDs and the third set of CIDs is unique. However, the first set of CIDs and the fourth set of CIDs include the common CID, i.e., the CID-1. Therefore, to avoid a conflict during handover between collocated BSs caused by the common CID, i.e., the CID-1, the first set of CIDs and the fourth set of CIDs are assigned to BS 804 and BS 810 since they are at maximum distance from each other. Thereafter, BS 804 allots the CID-1 to MS 812 and the CID-2 to MS 814 and BS 806 allots the CID-3 to MS 816 and the CID-4 to MS 818. Similarly, BS 808 allots the CID-5 to MS 820 and the CID-6 to MS 822 and BS 810 allots the CID-7 to MS 824 and the CID-1 to MS 826.

When MS 812 is handovered from BS 804 to BS 810, a conflict occurs because of the common CID, i.e., the CID-1, which is assigned to each of MS 812 and MS 826. In order to avoid this conflict, the CID-1 assigned to MS 826 served by BS 810 is replaced by the CID-5 assigned to the MS 820 served by BS 908. Therefore, the fourth set of CIDs is altered to include CID-7 and CID-5 to avoid any conflict during a handover.

Various embodiments of the invention provide a method and apparatus for managing a plurality of Connection Identifiers (CIDs) in a wireless communication network. In the present invention, a plurality of sets of CIDs are assigned to one or more BSs globally by an Access Service Network Gateway (ASN-GW). The plurality of sets of CIDs may be unique. In this case, the ASN-GW assigns the plurality of sets of CIDs irrespective of the distance between the one or more BSs. Alternatively, one or more CIDs in the plurality of sets of CIDs may be common. This facilitates the reuse of CIDs in the wireless communication network. In this case, the ASN-GW assigns the plurality of sets of CIDs based on the distance between the one or more BSs. In both the cases, as the ASN-GW centrally assigns the plurality of CIDs, therefore, the possibility of a conflict between the plurality of CIDs, when a MS is handovered from a serving BS to a target BS is reduced. However, if a conflict occurs during handover of a MS from a serving BS to a target BS, then the ASN-GW alters a set of CIDs assigned to the target BS. Also, since assigning of the plurality of CIDs is centrally executed by the ASN-GW instead of a BS, therefore time needed for handover of a MS from a serving BS to a target BS is reduced. As a result, consumption of air interface capacity required by the BS is also reduced.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element (s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The invention claimed is:

1. A method of managing communications in a wireless communications network, the method comprising:
   generating a plurality of sets of Connection Identifiers (CIDs) from multiple CIDs, a subset of the multiple CIDs being common in a subset of the plurality of sets and at least one of the multiple CIDs being absent in at least one of the plurality of sets of CIDs; and
   assigning the plurality of sets of CIDs to a plurality of Base Stations (BSs) based on a predefined condition.

2. The method of claim 1, wherein each CID in each of the plurality of sets of CIDs is unique.

3. The method of claim 1, wherein the predefined condition is a distance between the plurality of BSs.

4. The method of claim 3, wherein assigning the plurality of sets of CIDs includes:
   computing the distance between the plurality of BSs; and allotting at least one set of CIDs of the plurality of sets of CIDs to a set of BSs selected from the plurality of BSs, wherein the distance between the set of BSs is maximum and the at least one set of CIDs includes at least one common CID.

5. The method of claim 1, wherein an Access Network Gateway (ASN-GW) manages the multiple CIDs.

6. The method of claim 1, wherein at least one BS of the plurality of BSs manages the multiple CIDs.

7. The method of claim 1 further comprising altering a first set of CIDs of the plurality of sets of CIDs assigned to a target BS of the plurality of BSs in an event a Mobile Station (MS) of a plurality of MSs is handed-over from a serving BS of the plurality of BSs to the target BS, wherein a first CID of the first set of CIDs and a second CID assigned to the MS by the serving BS are the same.

8. The method of claim 7, wherein altering the first set of CIDs further includes replacing the first CID with a third CID selected from a second set of CIDs of the plurality of sets of CIDs assigned to a BS in the plurality of BSs.

9. The method of claim 8, wherein the distance between the target BS and the BS is maximum.

10. The method of claim 8, wherein the third CID in the second set of CIDs is unused.

11. The method of claim 1, wherein the wireless communications network is one of a WiMAX communication network, a 3rd Generation Partnership Project (3GPP) Long Term Evolution (LTE) network, a 3rd Generation Partnership Project 2 (3GPP2) Ultra Mobile Broadband (UMB) network, a Wireless Fidelity (WiFi) network, and an Orthogonal Frequency Division Multiple Access (OFDMA) communications network having a backhaul link.

12. A system for managing communication in a wireless communications network, the system comprising:
a generation module configured to generate a plurality of sets of CIDs from multiple CIDs, a subset of the multiple CIDs being common in a subset of the plurality of sets of CIDs and at least one of the multiple CIDs being absent in at least one of the plurality of sets of CIDs; and
an assignment module configured to assign the plurality of sets of CIDs to a plurality of Base stations (BSs) based on a predefined condition.

13. The system of claim 12, wherein the predefined condition is a distance between the plurality of BSs.

14. The system of claim 13, wherein the assigning module includes:
a computation module configured to compute the distance between the plurality of BSs; and
an allotment module configured to allot at least one set of CIDs of the plurality of sets of CIDs to a set of BSs selected from the plurality of BSs, wherein a distance between the set of BSs is maximum and the at least one set of CIDs includes at least one common CID.

15. The system of claim 12 further comprising an alteration module configured to alter a first set of CIDs of the plurality of sets of CIDs assigned to a target BS of the plurality of BSs in an event a Mobile Station (MS) of a plurality of MSs is handed-over from a serving BS of the plurality of BSs to the target BS, wherein a first CID of the first set of CIDs and a second CID assigned to the MS by the serving BS are the same.

16. The system of claim 15, wherein the alteration module further includes a replacement module configured to replace the first CID with a third CID selected from a second set of CIDs of the plurality of sets of CIDs assigned to a BS in the plurality of BSs, wherein the distance between the target BS and the BS maximum.

17. An apparatus for managing communication in a wireless communications network, the apparatus comprising:
a transceiver processor configured to:
generate a plurality of sets of CIDs from multiple CIDs a subset of the multiple CIDs being common in a subset of the plurality of sets and at least one of the multiple CIDs being absent in at least one of the plurality of sets of CIDs; and
assign the plurality of sets of CIDs to a plurality of Base Stations (BSs) based on a predefined condition; and
a transceiver configured to communicate the assignment of the plurality of sets of CIDs to a plurality of BSs in the wireless communications network.

18. The apparatus of claim 17, wherein the predefined condition is a distance between the plurality of BSs.

19. The apparatus of claim 18, wherein the transceiver processor is further configured to:
compute the distance between the plurality of BSs; and
allot at least one set of CIDs of the plurality of sets of CIDs to a set of BSs selected from the plurality of BSs, wherein the distance between the set of BSs is maximum and the at least one set of CIDs includes at least one common CID.

20. The apparatus of claim 17, wherein the transceiver processor is further configured to alter a first set of CIDs of the plurality of sets of CIDs assigned to a target BS of the plurality of BSs in an event a Mobile Station (MS) of a plurality of MSs is handed-over from a serving BS of the plurality of BSs to the target BS, wherein a first CID of the first set of CIDs and a second CID assigned to the MS by the serving BS are the same.

21. The apparatus of claim 20, wherein the transceiver processor is further configured to replace the first CID with a third CID selected from a second set of CIDs of the plurality of sets of CIDs assigned to a BS in the plurality of BSs, wherein the distance between the target BS and the BS maximum.

22. The apparatus of claim 17, wherein the apparatus is an Access Service Network Gateway (ASN-GW).

23. The apparatus of claim 17, wherein the apparatus is a BS of the plurality of BSs.

24. A method of managing communication in a wireless communications network, the method comprising:
assigning a plurality of sets of Connection Identifiers (CIDs) from multiple CIDs to a plurality of Base Stations (BSs) based on a predefined condition; and
inspecting the plurality of sets of CIDs assigned to the BSs and, in an event of a conflict, altering a CID of a set of CIDs.

25. The method of claim 24, wherein assigning the plurality of sets of CIDs includes:
computing a distance between the plurality of BSs; and
allotting at least one set of CIDs of the plurality of sets of CIDs to a set of BSs selected from the plurality of BSs, wherein the distance between the set of BSs is maximum and the at least one set of CIDs includes at least one common CID.

26. The method of claim 24, wherein an Access Network Gateway (ASN-GW) or a BS manages the multiple CIDs.

27. The method of claim 24, wherein altering the CID of the set of CIDs further includes altering a first set of CIDs assigned to a target BS and, in an event a Mobile Station (MS) of a plurality of MSs is handed-over from a serving BS to the target BS, wherein the first set of CIDs and a second set of CIDs assigned to the MS by the serving BS are the same.

28. The method of claim 27, wherein altering the CID of the set of CIDs further includes replacing the first CID with a third CID selected from a second set of CIDs of the plurality of sets of CIDs assigned to a BS in the plurality of BSs.

29. A system for managing communication in a wireless communications network, the system comprising:
   an assignment module configured to assign a plurality of sets of Connection Identifiers (CIDs) from multiple CIDs to a plurality of Base Stations (BSs) based on a predefined condition; and
   an inspection module configured to inspect the plurality of sets of CIDs assigned to the BSs and, in the event of a conflict, altering a CID of a set of CIDs.

30. The system of claim 29, wherein the assignment module is further configured to:
   compute a distance between the plurality of BSs; and
   allot at least one set of CIDs of the plurality of sets of CIDs to a set of BSs selected from the plurality of BSs, wherein the distance between the set of BSs is maximum and the at least one set of CIDs includes at least one common CID.

31. The system of claim 29, wherein an Access Network Gateway (ASN-GW) or a BS manages the multiple CIDS.

32. The system of claim 29, wherein the alteration module is further configured to alter a first set of CIDs assigned to a target BS and, in an event a Mobile Station (MS) of a plurality of MSs is handed-over from a serving BS to the target BS, wherein the first set of CIDs and a second set of CIDs assigned to the MS by the serving BS are the same.

33. The system of claim 32, wherein the alteration module is further configured to replace the first CID with a third CID selected from a second set of CIDs of the plurality of sets of CIDs assigned to a BS in the plurality of BSs.

\* \* \* \* \*